United States Patent
Drysdale et al.

(10) Patent No.: US 7,148,316 B2
(45) Date of Patent: Dec. 12, 2006

(54) HYDROXY AMIDE ACETALS

(75) Inventors: Neville Everton Drysdale, Newark, DE (US); Laura Ann Lewin, Greenville, DE (US); Robert John Barsotti, Franklinville, NJ (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/241,489

(22) Filed: Sep. 30, 2005

(65) Prior Publication Data
US 2006/0069266 A1   Mar. 30, 2006

Related U.S. Application Data

(60) Provisional application No. 60/615,360, filed on Sep. 30, 2004.

(51) Int. Cl.
*C08G 63/44* (2006.01)
*C08G 73/06* (2006.01)
*C08G 65/34* (2006.01)

(52) U.S. Cl. .......... 528/363; 528/44; 528/418; 528/423; 528/425; 528/354; 525/454; 525/528; 428/423.1

(58) Field of Classification Search .......... 528/44, 528/418, 423, 425, 363, 354; 525/454, 528; 428/423.1
See application file for complete search history.

(56) References Cited

U.S. PATENT DOCUMENTS

2005/0222425 A1* 10/2005 Adelman et al. .......... 548/218

* cited by examiner

*Primary Examiner*—Samuel A. Acquah
(74) *Attorney, Agent, or Firm*—Chyrrea J. Sebree

(57) ABSTRACT

The present invention relates to the preparation of hydroxy-functionalized amide acetals from bis-(beta hydroxy)amines and hydroxyl containing moieties.

3 Claims, No Drawings

HYDROXY AMIDE ACETALS

CROSS REFERENCE TO RELATED APPLICATION

This application claims the benefit of U.S. Provisional Application 60/615,360, filed Sep. 30, 2004.

FIELD OF THE INVENTION

The present invention relates to the preparation of hydroxy-functionalized amide acetals.

BACKGROUND OF THE INVENTION

Amide acetals have been used for example in copolymerization with polyisocyanates as disclosed in U.S. Pat. No. 4,721,767. Cross-linked amide acetal based coating compositions dry and cure rapidly without the potential problems created by VOC emissions. Such coatings can be very useful, for example, in the automotive coatings industry.

Co-owned and co-pending U.S. Patent Publication 2005-007461 describes polymeric compositions containing amide acetal groups, which are crosslinked by hydrolyzing the amide acetal groups, and subsequently reacting the hydroxyl groups and/or the amine functions that are formed to crosslink the composition.

Co-owned and co-pending U.S. patent application Ser. No. 10/960,656 describes a catalytic process for making amide acetals from nitrites and diethanolamines.

Hydroxy-functionalized amide acetals find use in crosslinkable coatings. CA 132: 280540, an anonymous disclosure, alluded to the potential preparation of hydroxy amide acetals from epoxides and oxazolines but did not include how to make these, nor provide any experimental results. However, the syntheses of these materials from hydroxy acids, esters or from lactone and beta-dihydroxyamines, has not be disclosed, nor has experimental data been shown elsewhere in support of the composition of these compounds.

SUMMARY OF THE INVENTION

The present invention relates to hydroxy amide acetals of the formula

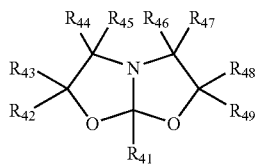

wherein $R_{42}$–$R_{49}$ independently represent a hydrogen, $C_1$–$C_{20}$ alkyl, $C_1$–$C_{20}$ alkenyl, $C_1$–$C_{20}$ alkynyl, $C_1$–$C_{20}$ aryl, $C_1$–$C_{20}$ alkyl ester, or $C_1$–$C_{20}$ aralkyl group, said alkyl, alkenyl, alkynyl, aryl, or aralkyl may each have one or more substituents selected from the groups consisting of halo, alkoxy, imino, and dialkylamino;

$R_{41}$ is $(CR_{50}R_{51})_n$—OH, wherein $R_{50}$ and $R_{51}$ independently represent a hydrogen, $C_1$–$C_{20}$ alkyl, $C_1$–$C_{20}$ alkenyl, $C_1$–$C_{20}$ alkynyl, $C_1$–$C_{20}$ aryl, $C_1$–$C_{20}$ alkyl ester, or $C_1$–$C_{20}$ aralkyl group; and n is 1–10.

The present invention further provides a process for forming a hydroxy amide acetal, said process comprising reacting a bis-(beta hydroxyl)amine with a hydroxy-containing moiety to form a hydroxy amide acetal of the formula

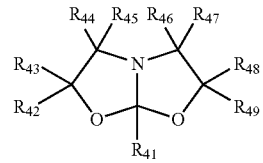

wherein $R_{42}$–$R_{49}$ independently represent a hydrogen, $C_1$–$C_{20}$ alkyl, $C_1$–$C_{20}$ alkenyl, $C_1$–$C_{20}$ alkynyl, $C_1$–$C_{20}$ aryl, $C_1$–$C_{20}$ alkyl ester, or $C_1$–$C_{20}$ aralkyl group, said alkyl, alkenyl, alkynyl, aryl, or aralkyl may each have one or more substituents selected from the groups consisting of halo, alkoxy, imino, and dialkylamino;

$R_{41}$ is $(CR_{50}R_{51})_n$—OH, wherein $R_{50}$ and $R_{51}$ independently represent a hydrogen, $C_1$–$C_{20}$ alkyl, $C_1$–$C_{20}$ alkenyl, $C_1$–$C_{20}$ alkynyl, $C_1$–$C_{20}$ aryl, $C_1$–$C_{20}$ alkyl ester, or $C_1$–$C_{20}$ aralkyl group; and n is 1–10.

The invention further relates to products made by the process disclosed.

DETAILS OF THE INVENTION

The present invention relates to a process for the preparation of hydroxy amide acetals. Amide acetals have the general formula

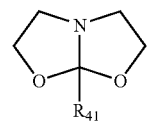

General processes for producing amide acetals are disclosed in co-owned and co-pending U.S. Patent Publication 2005-007461 and U.S. patent application Ser. No. 10/960,656. As disclosed in these applications, amide acetals can also be represented by the formula

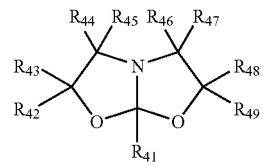

wherein $R_{42}$–$R_{49}$ independently represent a hydrogen, $C_1$–$C_{20}$ alkyl, $C_1$–$C_{20}$ alkenyl, $C_1$–$C_{20}$ alkynyl, $C_1$–$C_{20}$ aryl, $C_1$–$C_{20}$ alkyl ester, or $C_1$–$C_{20}$ aralkyl group, said alkyl, alkenyl, alkynyl, aryl, or aralkyl may each have one or more substituents selected from the groups consisting of halo, alkoxy, imino, and dialkylamino; and, $R_{41}$ is $(CR_{50}R_{51})_n$—OH, wherein $R_{50}$ and $R_{51}$ independently represent a hydrogen, $C_1$–$C_{20}$ alkyl, $C_1$–$C_{20}$ alkenyl, $C_1$–$C_{20}$ alkynyl, $C_1$–$C_{20}$ aryl, $C_1$–$C_{20}$ alkyl ester, or $C_1$–$C_{20}$ aralkyl group ; and where n is 1–10. It is more typical that $R_{42}$–$R_{49}$ each independently represent hydrogen and $C_1$–$C_{10}$ alkyl groups.

These and other features and advantages of the present invention will be more readily understood, by those of ordinary skill in the art, from a reading of the following detailed description. It is to be appreciated those certain features of the invention, which are, for clarity, described above and below in the context of separate embodiments, may also be provided in combination in a single embodiment. Conversely, various features of the invention that are, for brevity, described in the context of a single embodiment, may also be provided separately or in any sub-combination. In addition, references in the singular may also include the plural (for example, "a" and "an" may refer to one, or one or more) unless the context specifically states otherwise.

It has been discovered that hydroxy functionalized amide acetals are readily synthesized by reacting hydroxy-containing moieties, including but not limited to hydroxy acids, hydroxy esters or lactones, with beta-dihydroxyamines. More specifically, this involves reacting, for example, a bis-(beta hydroxy)amine of the general formula

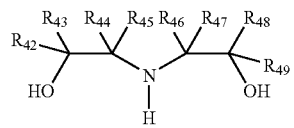

where $R_{42}$–$R_{49}$ are defined as above, with a hydroxy acid of the formula HO—$(CR_{50}R_{51})_n$—C(O)OH, where n is generally 1 to 10; or with a hydroxy ester of the formula HO—$(CR_5OR_{51})_n$—C(O)OR, where n is generally 1 to 10 and R is any $C_1$ to $C_{10}$ alkyl group;

or with a lactone of the formula

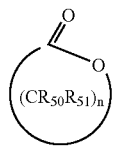

where n is 2 to 10;

to form

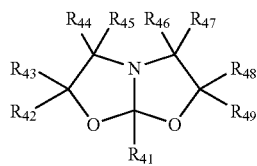

with all the R groups as defined above.

Generally, the reactants are added together with or without a common solvent (e.g., and heated to a gentle reflux until the reaction is complete (generally 12–24 hours) and the water formed by the reaction is distilled off and removed. If a solvent is used, it is desirable to use an azeotropic solvent such as xylenes or toluene.

The materials made by the process described find use in a variety of end-uses, including but not limited to components in coatings for automotive and architectural structures.

The use of numerical values in the various ranges specified in this application, unless expressly indicated otherwise, are stated as approximations as though the minimum and maximum values within the stated ranges were both preceded by the word "about." In this manner slight variations above and below the stated ranges can be used to achieve substantially the same results as values within the ranges. Also, the disclosure of these ranges is intended as a continuous range including every value between the minimum and maximum values.

Unless otherwise stated, all chemicals and reagents were used as received from Aldrich Chemical Co., Milwaukee, Wis.

EXAMPLES

Example 1

In a 500 mL RB flask equipped with a Dean Starke trap, glycolic acid (76.0 g, 1.00 mol), diisopropanolamine (133 g, 1.00 mol) and xylenes (100 mL) were added. The reaction content was heated to a gently reflux. After ~16 hours 22.73 g of water was collected. The trap was removed and the xylenes removed under vacuum and the reaction content vacuum distilled.

| Fraction | Weight | Comment |
| --- | --- | --- |
| 1 | 12.80 | Almost all product |
| 2 | 51.18 | Almost all product |
| 3 | 57.70 | almost all product |
| 4 | 31.58 | Contaminated product |

Example 2

In a 500 mL RB flask equipped with a Dean Starke trap, E-caprolactone (109.60, 0.96 mol), diisopropanolamine (129.9 g, 0.96 mol) and xylenes (100 mL) were added. The reaction content was heated to a gently reflux. After ~16 hours 3.92 g of water was collected. The trap was removed and the xylenes removed under vacuum and the reaction content vacuum distilled. NMR (proton) of the second fraction (47.22 g) showed it to contain product although contaminated.

What is claimed is:

1. A process for forming a hydroxy amide acetal, said process comprising reacting a bis-(beta hydroxyl)amine with a hydroxyl acid, hydroxyl ester or lactone to form a hydroxy amide acetal of the formula

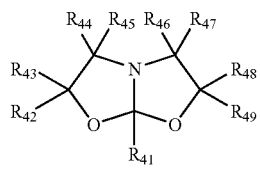

wherein $R_{42}$–$R_{49}$ independently represent a hydrogen, $C_1$–$C_{20}$ alkyl, $C_1$–$C_{20}$ alkenyl, $C_1$–$C_{20}$ alkynyl, $C_1$–$C_{20}$ aryl, $C_1$–$C_{20}$ alkyl ester, or $C_1$–$C_{20}$ aralkyl group, said alkyl, alkenyl, alkynyl, aryl, or aralkyl may each have one or more substituents selected from the groups consisting of halo, alkoxy, imino, and dialkylamino;

$R_{41}$ is $(CR_{50}R_{51})_n$—OH, wherein $R_{50}$ and $R_{51}$ independently represent a hydrogen, $C_1$–$C_{20}$ alkyl, $C_1$–$C_{20}$ alkenyl, $C_1$–$C_{20}$ alkynyl, $C_1$–$C_{20}$ aryl, $C_1$–$C_{20}$ alkyl ester, or $C_1$–$C_{20}$ aralkyl group; and n is 1–10.

2. The process of claim 1, wherein $R_{42}$–$R_{49}$ each independently represent hydrogen and $C_1$–$C_{10}$ alkyl groups.

3. A product of the process of claim 2.

* * * * *